United States Patent
Schenk

[11] Patent Number: 6,160,404
[45] Date of Patent: Dec. 12, 2000

[54] CIRCUIT FOR MEASURING THE ELECTRODE CURRENT OF A CERAMIC GAS SENSOR

[75] Inventor: Rene Schenk, Tamm, Germany

[73] Assignee: Robert Bosch GmbH, Stuttgart, Germany

[21] Appl. No.: 09/088,053

[22] Filed: Jun. 1, 1998

[30] Foreign Application Priority Data

May 31, 1997 [DE] Germany ............... 197 22 872

[51] Int. Cl.[7] ...................... G01N 27/62; G01N 27/00
[52] U.S. Cl. .................................. 324/464; 422/98
[58] Field of Search .................... 324/464, 71.1, 324/705, 691, 713, 468, 470, 717; 422/95, 98

[56] References Cited

U.S. PATENT DOCUMENTS

| | | | |
|---|---|---|---|
| 4,147,513 | 4/1979 | Bienkowski et al. | 324/71.1 |
| 4,233,033 | 11/1980 | Eifler et al. | 324/717 |
| 4,792,433 | 12/1988 | Katsura et al. | 422/98 |
| 5,054,452 | 10/1991 | Denz . | |

*Primary Examiner*—Safet Metjahic
*Assistant Examiner*—Anjan K Deb
*Attorney, Agent, or Firm*—Walter Ottesen

[57] ABSTRACT

The invention relates to a circuit for measuring the electrode current of a ceramic gas sensor for measuring a gas. The ceramic gas sensor has first and second sensor electrodes arranged in a heatable ceramic and the first sensor electrode functions as a measuring electrode and the second sensor electrode functions as a reference electrode. The circuit is a current measuring circuit connected to the first and second sensor electrodes and the current measuring circuit includes: a current measuring shunt (R2) for conducting a measurement current flowing away from the first sensor electrode thereby causing a first voltage drop across the current measuring shunt (R2); a first circuit part for detecting the measurement current; a current feedback shunt (R1) connected to the second sensor electrode; a second circuit part for generating a current having a magnitude corresponding to the magnitude of the measurement current detected by the first circuit part; the second circuit part being connected to the current feedback shunt (R1) whereby the current generated by the second circuit part flows to the second sensor electrode via the current feedback shunt (R1) causing a second voltage drop across the current feedback shunt (R1); and, a third circuit part for amplifying the difference of the first and second voltage drops and converting the difference into a measurement signal referred to a reference potential.

5 Claims, 6 Drawing Sheets

6,160,404

CIRCUIT FOR MEASURING THE ELECTRODE CURRENT OF A CERAMIC GAS SENSOR

FIELD OF THE INVENTION

The invention relates to a circuit for measuring the electrode current of a ceramic gas sensor having two sensor electrodes arranged in a heatable ceramic. One of the electrodes is arranged in the gas the composition of which is to be detected and the other sensor electrode functions as a reference electrode. The electrode current is measured by a current measuring circuit connected downstream of the sensor electrodes of the gas sensor.

BACKGROUND OF THE INVENTION

Ceramic gas sensors of this kind have been known for a long time. These gas sensors are preferably utilized in automobiles for detecting toxic exhaust gases and have an ion-conducting ceramic such as zirconium oxide ($ZRO_2$). The ceramic must be heated in order to ensure a proper operation. For this reason, a heater is embedded in the ceramic. The heater must be insulated because the ceramic is electrically conductive in the heated operational state.

The insulation of the heater is, however, problematic (especially at high temperatures) because leakage resistances result from the heater to the sensor electrodes in the order of magnitude of several megaohms.

This is non-critical in probes having high measuring currents, such as lambda probes. However, for gas sensors wherein the measuring effect lies in the order of magnitude of several microamperes and which gas sensors must be operated in combination with circuits which evaluate the current, a very large measurement error occurs. The leakage current flowing away from the heater is superposed on the actual measuring current and causes relatively large errors in the measurement result.

Large differences occur with respect to individual gas sensors and a very significant deterioration occurs. For this reason, the leakage current cannot be simply compensated by a fixed corrective quantity.

For the above reason, an isolation amplifier has, for example, been used up to now for measuring the measurement current. Because of the isolation amplifier, the actual measuring circuit is driven separately with respect to potential and the measurement quantity is transmitted in an insulated manner for further signal processing. The potential partition can, for example, be achieved with a transformer or optoelectronically. In this case, the voltage potential at the sensor electrodes so adjusts that the leakage current becomes zero because this leakage has nowhere to flow to. The consequence thereof is that only the desired measuring current is measured. It is disadvantageous in this measurement method that there is a high requirement of expensive components which cannot be integrated or can be integrated only with difficulty.

For sensors which supply a voltage signal, it is known to make the measurement via a so-called electrometer or instrument amplifier. This amplifier measures the voltage "without current" so that a leakage current has no effect on the measurement result.

U.S. Pat. No. 5,054,452 discloses a method and an arrangement for detecting a fault condition of a lambda probe and measures are taken as a consequence of a fault signal which is outputted when a fault condition is detected. In this method, impermissibly large fault causes can be diagnosed during operation of the lambda probe utilizing a correlation method. Shunts exist only during operation of the heater. For this reason, the probe heater is switched off in this measurement method for detecting a fault condition because, in this case, no shunt voltage and therefore no falsification of the measurement result is present. The difference between the probe voltage measured for a switched-on heater and measured for a switched-off heater is the shunt voltage.

It is problematic in this method that it cannot be easily applied to a current measurement.

SUMMARY OF THE INVENTION

It is an object of the invention to provide a circuit for measuring the electrode current of a ceramic gas sensor which is so improved that the circuit permits a most precise detection of the measurement current without disturbances caused by leakage currents.

The circuit of the invention is for measuring the electrode current of a ceramic gas sensor for measuring a gas. The ceramic gas sensor has first and second sensor electrodes arranged in a heatable ceramic and the first sensor electrode functions as a measuring electrode and the second sensor electrode functions as a reference electrode. The circuit is a current measuring circuit connected to the first and second sensor electrodes and the current measuring circuit includes: a current measuring shunt (R2) for conducting a measurement current flowing away from the first sensor electrode thereby causing a first voltage drop across the current measuring shunt (R2); a first circuit part for detecting the measurement current; a current feedback shunt (R1) connected to the second sensor electrode; a second circuit part for generating a current having a magnitude corresponding to the magnitude of the measurement current detected by the first circuit part; the second circuit part being connected to the current feedback shunt (R1) whereby the current generated by the second circuit part flows to the second sensor electrode via the current feedback shunt (R1) causing a second voltage drop across the current feedback shunt (R1); and, a third circuit part for amplifying the difference of the first and second voltage drops and converting the difference into a measurement signal referred to a reference potential.

The first circuit part detects the measuring current flowing from the first sensor electrode and the second circuit part generates a current which has the same magnitude as the detected measurement current and flows to the other sensor electrode. With these first and second circuit parts, the situation is advantageously achieved that the measurement current, which flows from the first sensor electrode of the sensor element, flows with the same magnitude into the second sensor electrode. The invention is based on the idea that, when these two currents are exactly equal, a leakage current leads to a shift of the measurement potential at the sensor electrodes only until the leakage current becomes zero.

The third circuit part amplifies the voltage difference dropping across the shunt resistors. Here, the actual measurement quantity is then converted in an especially simple manner into a measurement signal referred to a reference potential.

In principle, the most different embodiments are conceivable with respect to the configuration of the circuit parts.

An advantageous embodiment can be realized in a simple manner especially as an integrated circuit. This advantageous embodiment provides that the first circuit part includes a first operational amplifier wired as an inverting current-voltage converter. The current measuring shunt is connected into the feedback branch of this operational amplifier. This advantageous embodiment further provides that the second circuit part includes a second operational amplifier connected downstream of the first operational amplifier as a voltage inverter. This operational amplifier inverts the output voltage of the first operational amplifier with respect to the reference potential. The output voltage of the second operational amplifier drops across the current return shunt to generate the return flowing measuring current. This embodiment further provides that the third circuit part includes a third operational amplifier connected as a difference amplifier.

Disturbances can be caused by long supply lines and, to compensate for these disturbances, an advantageous embodiment of the invention provides that a capacitor is connected between the inverting input of the first operational amplifier and the output thereof and that an ohmic resistance is connected forward of the inverting input of the first operational amplifier. With this circuitry of the first operational amplifier, the measuring circuit is especially insensitive with respect to high disturbance frequencies.

For some sensor types, the current measurement must take place with an applied bias voltage. For a defined bias voltage, defined individual gas components can be detected because the gas sensor is driven as a pump cell in this case.

In order to operate the current measuring circuit at a defined bias voltage, an advantageous embodiment of the invention provides that a voltage divider downstream of impedance converters is connected forward of the current measuring circuit. With this voltage divider, the reference potential of the current measuring circuit is shifted via a desired voltage source connected downstream of the voltage divider.

The desired voltage source can be realized in many different ways. For example, a Zener diode can be provided therefor. An advantageous embodiment provides that the desired voltage source includes a resistor through which current from the output signal of a current source flows. This embodiment makes possible especially a drivable desired voltage source. In the above way, the desired voltage source can be adjusted, that is, the voltage superposed on the desired voltage source can be controlled.

BRIEF DESCRIPTION OF THE DRAWINGS

The invention will now be described with reference to the drawings wherein.

DESCRIPTION OF THE PREFERRED
EMBODIMENT OF THE INVENTION

Figure 1:
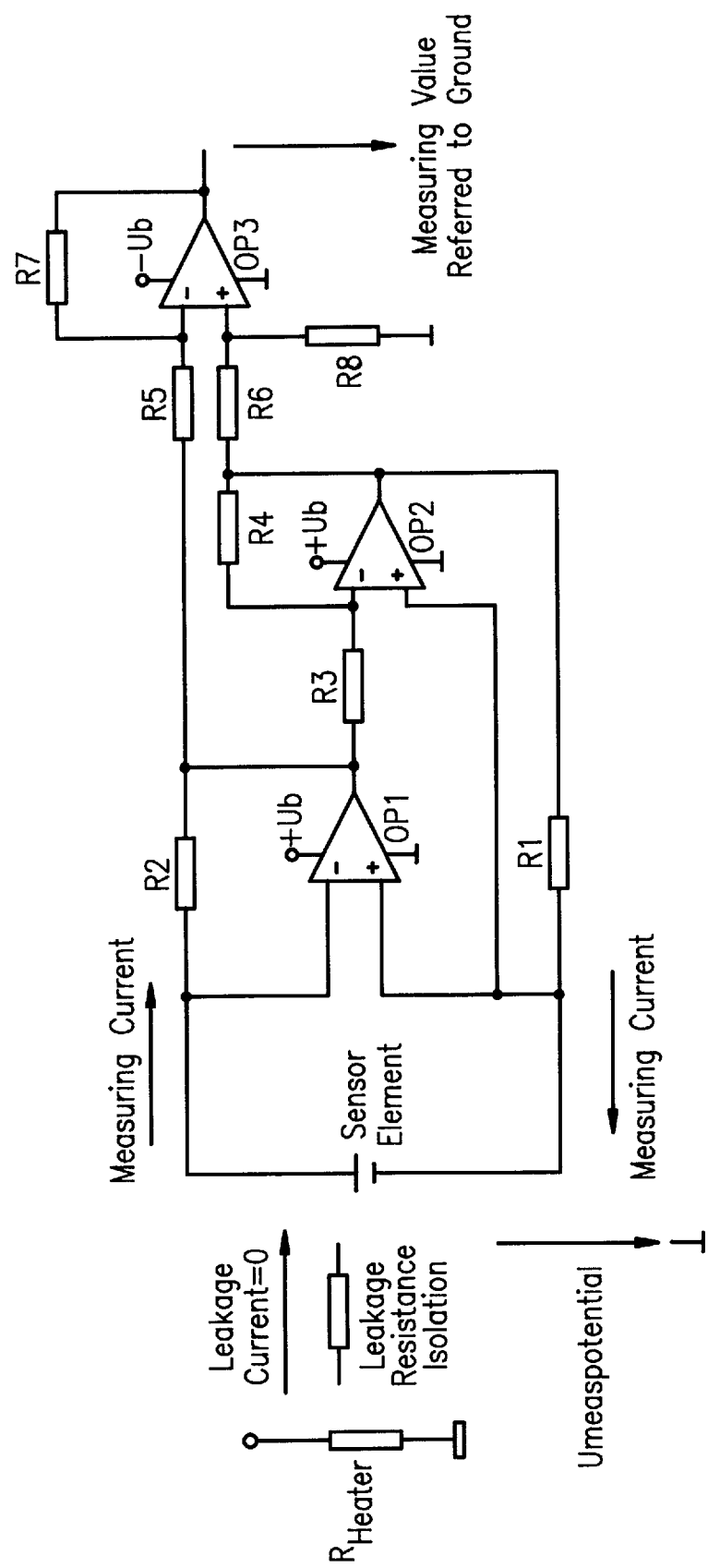
FIG. 1 is a schematic of a circuit according to the invention for measuring the electrode current of a ceramic gas sensor.

A current measuring circuit for measuring the electrode current of a ceramic gas sensor (not shown) is shown in FIG. 1 and includes three circuit parts. The gas sensor is heated via a heater resistor.

The first circuit part includes a first operational amplifier OP1 which is configured as an inverting current-voltage converter and controls the voltage between the two sensor terminals (that is, sensor electrodes) of the sensor element to zero. The current needed for this purpose generates a voltage drop in a current measuring shunt R2. This voltage drop is a measure of the measuring current. This voltage is inverted with respect to the potential of the second sensor terminal by an operational amplifier OP2 which is a component of a second circuit part.

The inverted voltage is connected via a current feedback shunt R1 to the second sensor terminal. In this way, the precise same voltage drop occurs at both shunt resistors R1 and R2. The same current flows in both circuit parts when both resistors are of the same magnitude or are adapted to the ratio of the resistors R3 and R4. Stated otherwise, a current, which corresponds to the current flowing away from the first measuring or sensor electrode (and which is detected by the first operational amplifier OP1) flows in the same magnitude into the second sensor electrode. In this way, a leakage current, which flows away from the heater, only leads to a shift of the measuring potential on the sensor electrode. This shift takes place until the leakage current vanishes.

Errors arise in this circuit only from pairing tolerances of the resistors and from the offset voltage of the operational amplifiers (OP1, OP2). However, these errors can at a maximum only be a small fraction of the measuring current and are therefore negligible.

The voltage drop across the two shunt resistors R1 and R2 is amplified via a third operational amplifier OP3 which is a component of a third circuit part. The third operational amplifier OP3 is connected as a difference amplifier.

Figure 2:
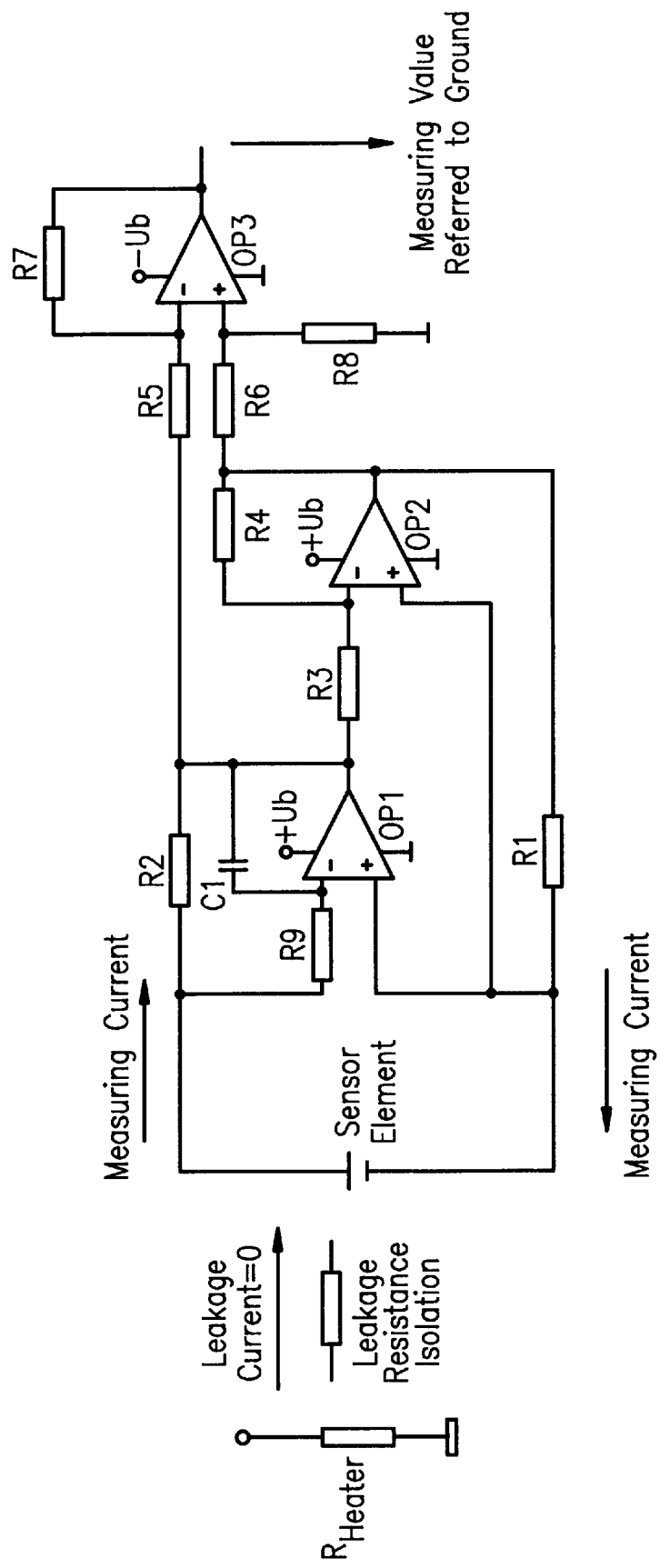
FIG. 2 is a schematic of a circuit according to a second embodiment of the invention for measuring the electrode current of a ceramic gas sensor.

The circuit shown in FIG. 2 differs from that shown in FIG. 1 only in that a capacitor C1 is connected between the inverting input and the output of the first operational amplifier OP1 and that an ohmic resistor R9 is connected in series with the inverting input of the first operational amplifier OP1.

The remaining elements of the circuit shown in FIG. 2 correspond to those of the circuit shown in FIG. 1 and reference is made to FIG. 1 with respect to the description thereof.

The circuit configuration of the first operational amplifier OP1 shown in FIG. 2 is based on the idea to make the circuit insensitive with respect to oscillations which can arise especially for a connection of the circuit with long feed lines and the capacitance which arises as a consequence thereof.

The circuit shown in FIG. 2 performs in DC operation as does the circuit shown in FIG. 1. The resistor R9 has no effect because the input current of the operational amplifier OP1 is almost zero. At higher frequencies, the circuit, however, becomes insensitive because of the negative feedback via capacitor C1. The amplification for high frequencies becomes low and the control loop therefore is stable.

For some types of gas sensors, the current measurement must take place with an applied bias voltage, for example, in order to detect different gas types. These gas types can be "pumped" away when applying a specific bias voltage.

Figure 3:
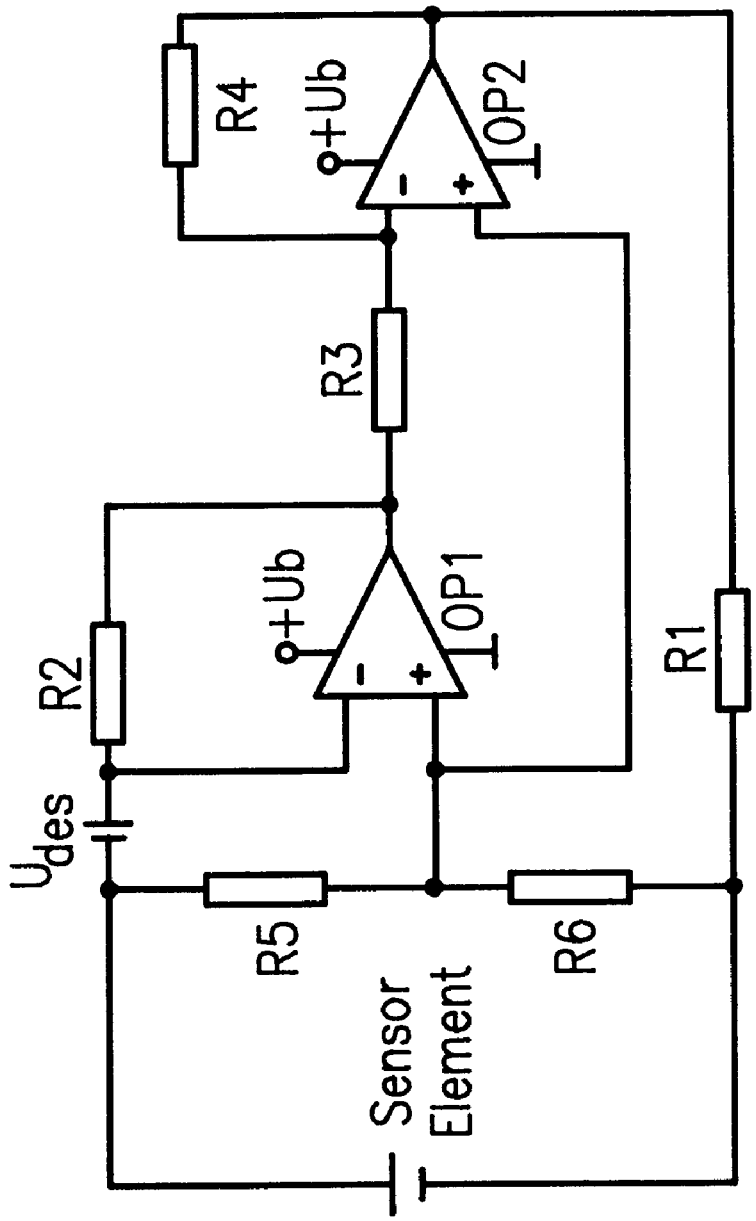
FIG. 3 is a schematic of a circuit according to a third embodiment of the invention for measuring the electrode current of a ceramic gas sensor.

A current measuring circuit is shown schematically in FIG. 3. With an applied bias voltage, this current measuring circuit makes possible that the measuring current, which flows away from the one sensor electrode, is of the same magnitude and flows to the other sensor electrode of the sensor element.

In the circuit shown in FIG. 3, a voltage divider of resistors R5 and R6 is connected downstream of the sensor electrodes. The voltage divider is connected in series with the first operational amplifier OP1 via a desired voltage source Udes. The operational amplifier OP1 controls the mid voltage via the current measuring shunt R2 such that the voltage drop across resistor R5 is equal to the desired voltage Udes which is generated by the desired voltage source Udes. The second operational amplifier OP2 mirrors the output voltage of the first operational amplifier OP1 with respect to the mid voltage of the voltage divider. In this way, the same voltage drop results at the current feedback shunt R1 as at the current measuring shunt R2. In the result, and as mentioned above, the two currents are in magnitude the same so that a leakage current can only lead to a shift of the measuring potential until the leakage current vanishes. The two currents flow away from the first sensor electrode and flow toward the second sensor electrode.

The measuring signal can also here be converted into a signal referred to ground via third operational amplifier OP3 (not shown in FIG. 3). The third operational amplifier OP3 is configured as a difference amplifier.

It is understood that the voltage divider and the desired voltage source can also be connected in series with the circuit shown in FIG. 2. Such a circuit is shown in FIGS. 4a and 4b.

Figure 4A:
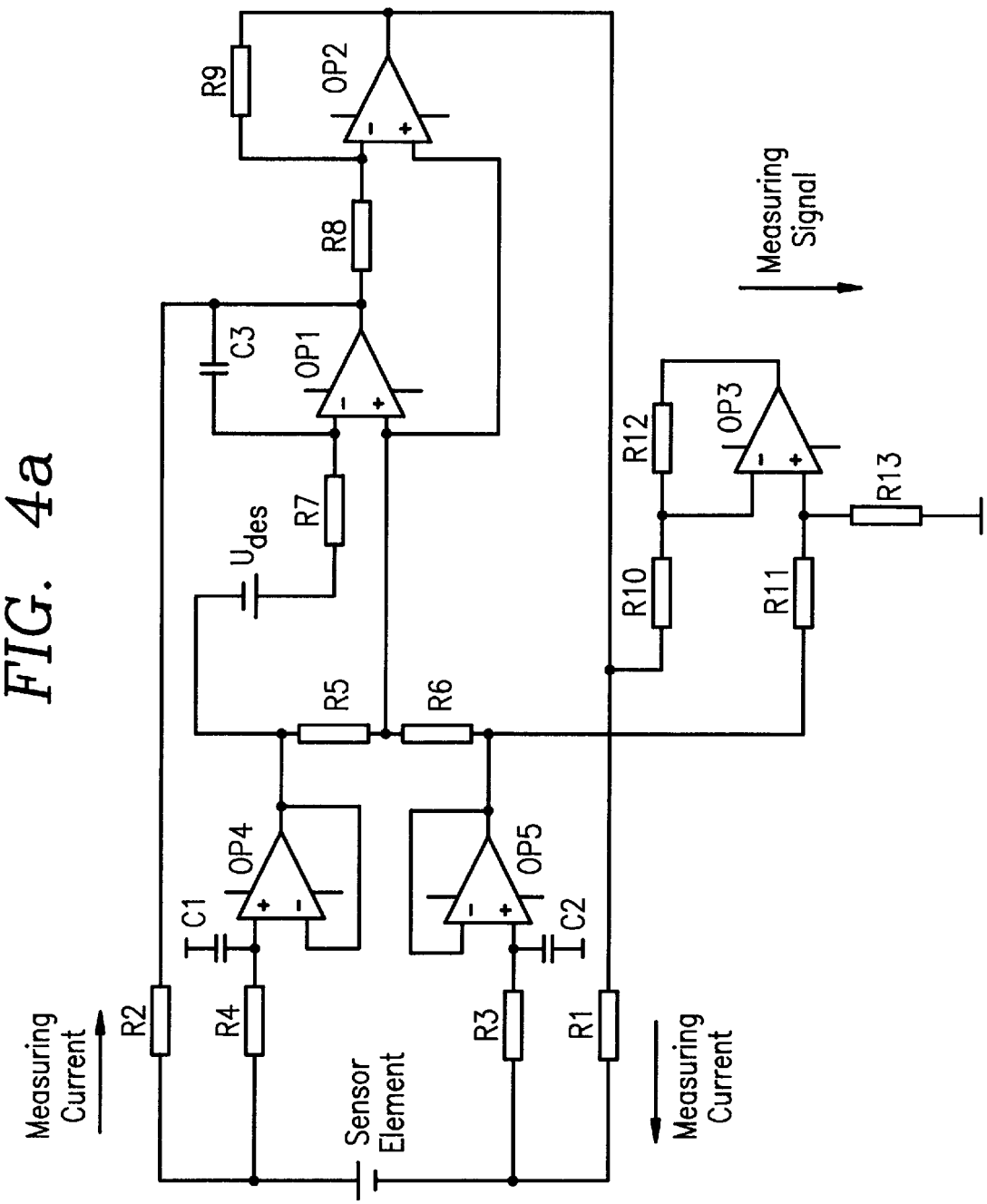
FIGS. 4A and 4B are a modification of the embodiment shown in FIG. 3 of a circuit for measuring the electrode current of a ceramic gas sensor; and, FIG. 5 is still another embodiment of the circuit of the invention for measuring the electrode current of a ceramic gas sensor.
Figure 4B:
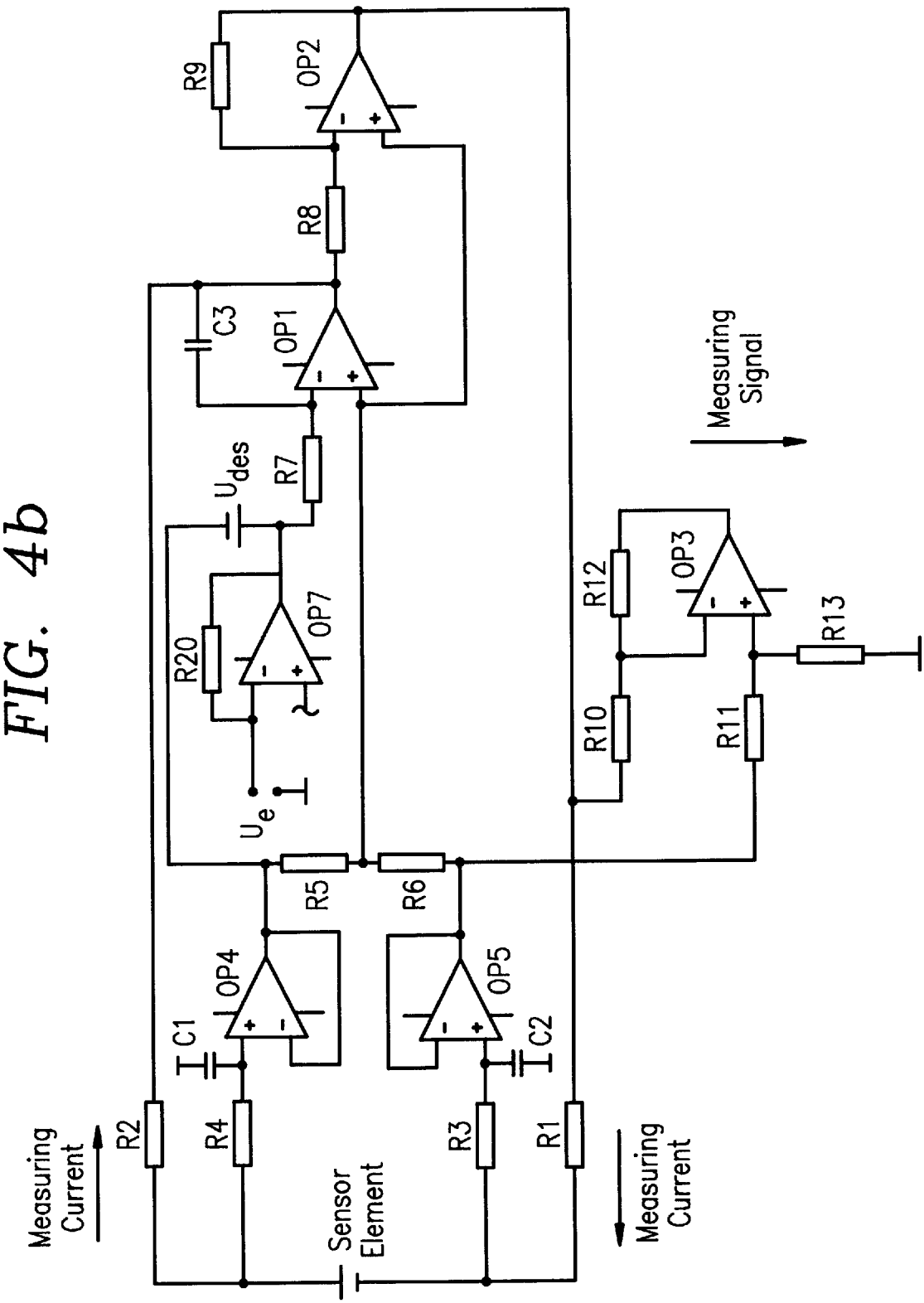

In addition to the circuit shown in FIG. 3, FIGS. 4a and 4b show respective impedance converters connected in series with the voltage divider of resistors R5 and R6.

As shown in FIGS. 4a and 4b these impedance converters are, for example, realized by operational amplifiers OP4 and OP5 both connected as impedance converters. The sensor voltage is first impedance converted by the impedance converters OP4 and OP5. The mid voltage between the outputs of the operational amplifiers OP4 and OP5 is generated by the resistors R5 and R6. The operational amplifier OP1 controls the mid voltage via the current measuring shunt R2 such that the voltage drop across R5 is equal to the desired voltage.

The operational amplifier OP1 is connected together with the capacitor C3 to define an I-controller. The operational amplifier OP2 mirrors the output voltage of the operational amplifier OP1 with respect to the shifted mid voltage. In this way, the same voltage drop occurs at the current feedback shunt R1 as at the current feedback shunt R2 so that the measuring current, which flows from the circuit to a sensor electrode, has the same magnitude as the measuring current which flows from the other sensor electrode into the circuit.

The measuring signal is, in turn, converted by the operational amplifier OP3 into a signal referred to ground. The operational amplifier OP3 is configured as a difference amplifier.

The desired voltage Udes can be realized in various ways, for example, via a Zener diode or the like. It is also possible to use a resistor as a desired voltage source. An output signal from a drivable current source flows through this resistor. With a desired voltage source of this kind, the superposed desired voltage can be controlled. This superposed desired voltage serves to shift the voltage. The desired voltage source (Udes) can also be realized by a resistor through which the output signal of a control current source flows as shown in FIGS. 4a and 4b. The controllable current source includes an inverter OP7 having feedback resistor R20.

In addition, sensor types are known for which a voltage measurement is used for evaluation but which require a superposed current. In principle, the same problems occur for the evaluation as with the current measurement.

Figure 5:
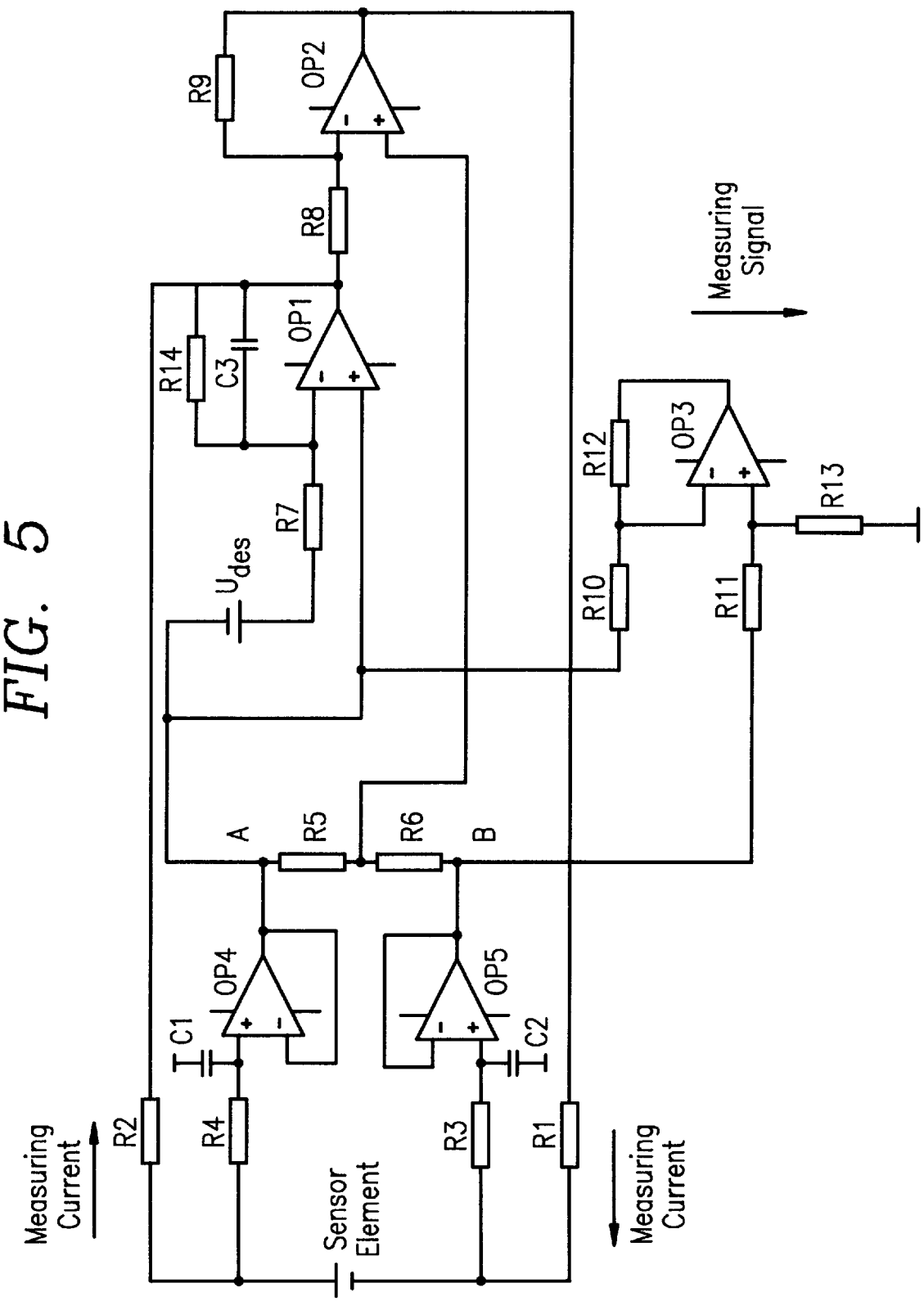

In order to obviate the above, the circuits shown in FIGS. 4a and 4b can be modified as shown in FIG. 5. The elements in FIG. 5 which are the same as those in FIGS. 4a and 4b are provided with the same reference numerals so that reference can be made to the description of FIGS. 4a and 4b as to an explanation of these circuit elements.

The circuit shown in FIG. 5 makes possible a high ohmic voltage measurement with superposed current. In this case, the operational amplifier OP1 adjusts a voltage at the current measuring shunt R2 which is greater than the voltage at the sensor terminal by the desired voltage Udes. The result is a superposed current. The operational amplifier OP2 here mirrors the voltage with respect to the shifted mid voltage and, on the current feedback shunt R1, generates a current of the same magnitude flowing in the opposite direction. Accordingly, here too, the measuring current, which flows from one sensor electrode into the circuit, again flows out of the circuit and to the other sensor electrode.

The circuits shown in FIGS. 2, 4a, 4b and 5 can also be used together with a measurement of the sensor resistor via an alternating voltage. With the filter measures described above in combination with FIG. 2, the circuits are not disturbed when coupling in an alternating voltage of adequately high frequency to the sensor element. This is necessary when temperature control of the sensors is intended to take place via the dynamic internal impedance.

It is especially advantageous that the circuits described above can be realized with especially simple components which can be integrated.

It is understood that the foregoing description is that of the preferred embodiments of the invention and that various changes and modifications may be made thereto without departing from the spirit and scope of the invention as defined in the appended claims.

What is claimed is:

1. A circuit for measuring the electrode current of a ceramic gas sensor for measuring a gas, the ceramic gas sensor having first and second sensor electrodes arranged in a heatable ceramic, the first sensor electrode functioning as a measuring electrode and the second sensor electrode functioning as a reference electrode, the circuit being a current measuring circuit connected to said first and second sensor electrodes and said current measuring circuit comprising:

a current measuring shunt (R2) for conducting a measurement current flowing away from said first sensor electrode thereby causing a first voltage drop across said current measuring shunt (R2);

a first circuit part for detecting said measurement current;

a current feedback shunt (R1) connected to said second sensor electrode;

a second circuit part for generating a current having a magnitude corresponding to the magnitude of said measurement current detected by said first circuit part; said second circuit part being connected to said current feedback shunt (R1) whereby said current generated by said second circuit part flows to said second sensor electrode via said current feedback shunt (R1) causing a second voltage drop across said current feedback shunt (R1); and, a third circuit part for amplifying the difference of said first and second voltage drops and converting said difference into a measurement signal referred to a reference potential.

2. The circuit of claim 1, wherein:

said first circuit part includes a first operational amplifier (OP1) wired as an inverting current-voltage converter having a feedback branch incorporating said current measuring shunt (R2);

said second circuit part including a second operational amplifier (OP2) connected in series with said first operational amplifier (OP1) and said second operational amplifier (OP2) being a voltage inverter for inverting the output voltage of said first operational amplifier (OP1) with respect to a reference potential;

said second operational amplifier (OP2) having an output voltage which drops across said current feedback shunt (R1) to generate current flowing back through said current feedback shunt (R1); and, said third circuit part including a third operational amplifier wired as a difference amplifier for amplifying the difference voltage dropping across said shunts (R1, R2).

3. The circuit of claim 2, further comprising: a capacitor (C1) connected between the inverting input and the output of said first operational amplifier (OP1); and, an ohmic resistor (R9) connected in series with the inverting input of said first operational amplifier (OP1).

4. The circuit of claim 3, further comprising:

a voltage divider (R5, R6) connected in series with said current measuring circuit and downstream of impedance converters; and, a desired voltage source (Udes) connected downstream of said voltage divider (R5, R6) to shift the reference voltage of the current measuring circuit.

5. The circuit of claim 4, said desired voltage source (Udes) being a resistor through which the output signal of a controllable current source flows.

* * * * *